United States Patent [19]

Takayanagi et al.

[11] Patent Number: 5,149,843
[45] Date of Patent: Sep. 22, 1992

[54] CONJUGATED DIENE COMPOUNDS

[75] Inventors: Hisao Takayanagi; Yasunori Kitano, both of Yokohama; Yasuhiro Morinaka, Tsuchiura, all of Japan

[73] Assignee: Mitsubishi Kasei Corporation, Tokyo, Japan

[21] Appl. No.: 712,043

[22] Filed: Jun. 7, 1991

[30] Foreign Application Priority Data

Jun. 20, 1990 [JP] Japan .................................. 2-162438

[51] Int. Cl.⁵ .................... C07C 33/02; C07C 33/14; C07C 33/42; C07C 43/15; C07C 43/17; C07C 49/203; C07C 49/24; C07D 303/08
[52] U.S. Cl. .................................. 549/561; 549/416; 549/420; 549/423; 549/554; 556/449; 556/482; 558/51; 558/52; 560/106; 560/111; 560/112; 560/113; 560/249; 560/261; 560/262; 568/376; 568/379; 568/415; 568/496; 568/497; 568/596; 568/598; 568/832; 568/838; 568/843; 568/849; 568/857; 568/975; 568/909.5
[58] Field of Search .................... 568/875, 909.5, 857, 568/596, 598, 832, 839, 843, 849, 415, 376, 379, 496, 497; 549/416, 420, 423, 554, 561; 558/51, 52; 556/449, 482; 560/106, 111, 112, 113, 249, 261, 212

[56] References Cited

U.S. PATENT DOCUMENTS 4,399,301  8/1983  Morel .............................. 502/909.5
4,906,794  3/1990  Umezu et al. ...................... 560/249
4,925,991  5/1990  MacKenroth et al. ........... 568/909.5

OTHER PUBLICATIONS

McMurry et al, "Tetrohydron Letters", vol. 30, No. 10, pp. 1173-1176, 1989.
Tetrahedron Letters, vol. 31, No. 23, pp. 3317-3320, 1990.

Primary Examiner—J. E. Evans
Attorney, Agent, or Firm—Wenderoth, Lind & Ponack

[57] ABSTRACT

Conjugated diene compounds of the general formula:

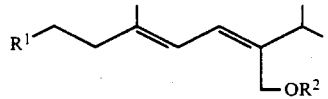

which are industrially advantageous intermediates for preparing sarcophytol A useful as an anticarcinogenic promotor or antitumor agent are provided.

1 Claim, No Drawings

CONJUGATED DIENE COMPOUNDS

The present invention relates to novel conjugated diene compounds. More particularly, the present invention is directed to conjugated diene compounds which are important intermediates for synthesis of sarcophytol A having anticarcinogenic promotor activity [Cancer Surveys, 2. 540 (1983): Taisha (Metabolism), Vol. 25, Extra Issue, Gan (Tumor), '88, 3 (1988)] and antitumor activity (Japanese Patent Publication (Examined) No. 20213/1988).

Sarcophytol A of the following structure is a cembrane type diterpene-alcohol having four double bonds in total, inclusive of one conjugated double bond in the fourteen membered ring.

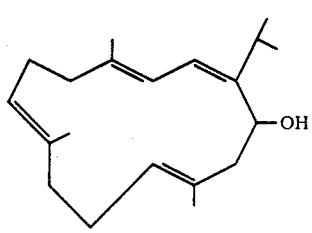

Sarcophytol A

No synthetic method of sarcophytol A has long been known. However, the present inventors recently proposed a synthetic route of sarcophytol A starting from the sesquiterpenoid as shown in the following Synthetic Route I via the key intermediate (E) (Japanese Patent Application No. 181710/1989).

Synthetic Route 1

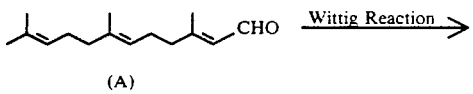
(A)

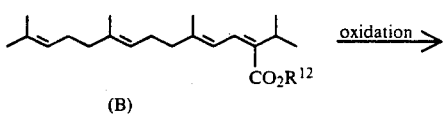
(B)

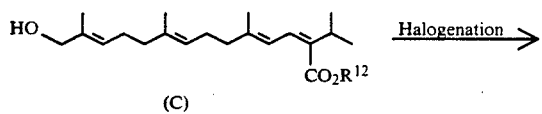
(C)

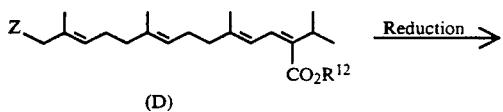
(D)

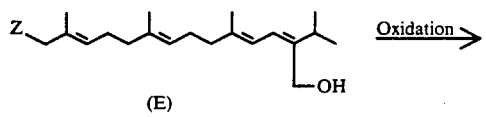
(E)

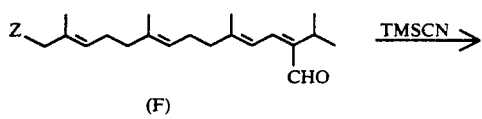
(F)

-continued
Synthetic Route 1

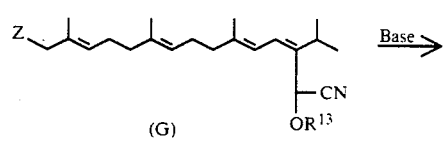
(G)

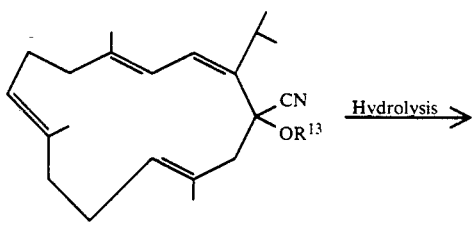
(H)

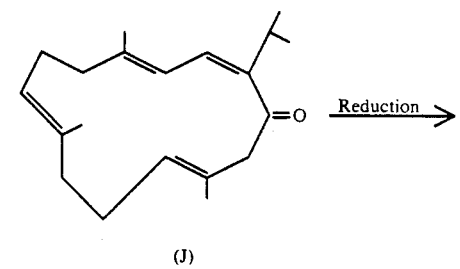
(J)

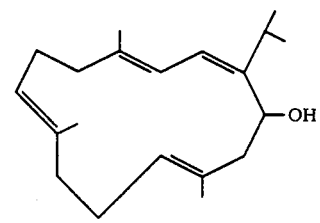

Sarcophytol A

In the above formula, $R^{12}$ is $C_1$-$C_4$ lower alkyl group, $R^{13}$ is trimethylsilyl group, 1-ethoxyethyl group or hydrogen atom, an Z is a leaving group such as halogen atom (e.g., chlorine, bromine or the like) or $-OSO_2R^6$ (in which $R^6$ is lower alkyl group such as methyl group, ethyl group or the like, halogen-substituted alkyl group, phenyl group or alkyl-substituted phenyl group, such as tolyl group or the like).

Industrial production of sarcophytol A according to the above Synthetic Route 1, however, has a big problem in the following points. First, expensive E, E-farnesal having a particular steric configuration, which is required for the synthesis of sarcophytol A, is needed in the preparation of the key intermediate (E). Second, for the production of the intermediate (E), Compound (B) must be subjected to oxidation of the terminal E-side methyl group with selenium oxide, which process is poor in yield and selectivity.

As the result of various investigations for resolving the above problems and providing an industrially advantageous synthetic route for preparing sarcophytol A, the present inventors have found that a class of conjugated diene compounds are very useful intermediates for the production of Compound (E) in the Synthetic Route 1 of sarcophytol A. The present invention has been established on the basis of such finding.

Thus, the present invention provides a class of conjugated diene compounds of the following general formula (I):

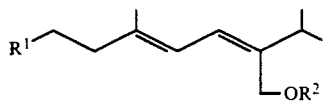

wherein $R^1$ is

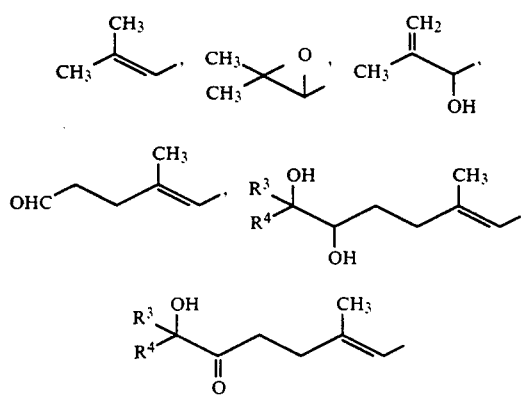

(in which $R^3$ and $R^4$ are independently alkyl group of 1 to 4 carbon atoms or taken together form alkyl group),

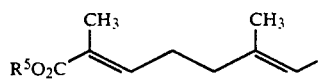

(in which $R^5$ is alkyl group of 1 to 4 carbon atoms)

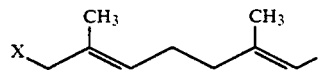

(in which X is hydroxy group, halogen atom or —O-SO$_2$R$^6$ (R$^6$ is alkyl group of 1 to 4 carbon atoms optionally substituted by halogen atom or phenyl group optionally substituted by alkyl group of 1 to 4 carbon atoms)), and $R^2$ is hydrogen atom,

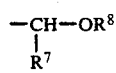

(in which $R^7$ is hydrogen atom or alkyl group of 1 to 4 carbon atoms, $R^8$ is alkyl group of 1 to 4 carbon atoms, or $R^7$ and $R^8$ taken together may form a ring),

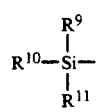

(in which $R^9$-$R^{11}$ are independently alkyl group of 1 to 4 carbon atoms or phenyl group) or acyl group, with the proviso that when $R^1$ is

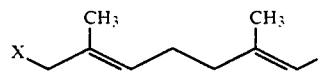

and X is a substituent other than hydroxy group, $R^2$ is not hydrogen atom,

The present invention will be explained below in detail.

In the formula (I), $R^1$ is

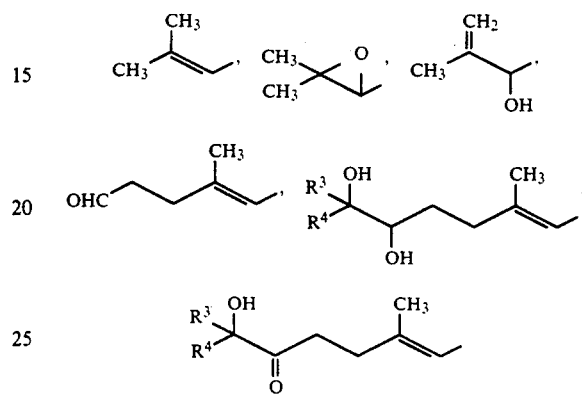

wherein $R^3$ and $R^4$ are independently alkyl group of 1 to 4 carbon atoms such as methyl group, ethyl group or the like, or taken together form cyclic alkyl group such as cyclohexyl group or the like,

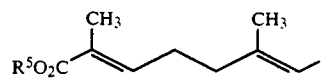

wherein $R^5$ is alkyl group of 1 to 4 carbon atoms such as methyl group, ethyl group or the like, or

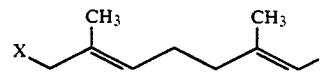

wherein X is hydroxy group, halogen atom such as chlorine atom, bromine atom or the like, or —OSO$_2$R$^6$ (R$^6$ is alkyl group of 1 to 4 carbon atoms optionally substituted by halogen atom such as methyl group, ethyl group, trifluoromethyl group or the like, or phenyl group optionally substituted by alkyl group, such as phenyl group, tolyl group or the like. $R^2$ includes hydrogen atom, methoxymethyl group, 1-ethoxyethyl group, tetrahydropyranyl group, tetrahydrofuranyl group, trimethylsilyl group dimethyl-t-butylsilyl group, diphenyl-ti-butylsilyl group, acetyl group, benzoyl group and the like. However, when $R^1$ is

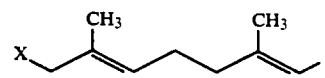

and X is a substituent other than hydroxy group, $R^2$ is not hydrogen atom.

Specific examples of the compounds of the general formula (I) are shown below.

(1) When $R^1$ is:

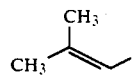

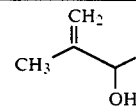

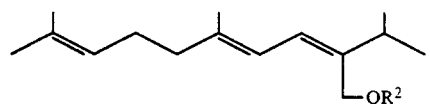

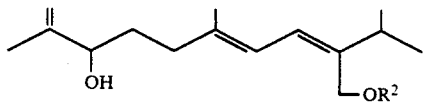

| Compound No. | $R^2$ |
|---|---|
| 1 | —H |
| 2 | —CHOC$_2$H$_5$ / C$_2$H$_5$ (=EE) |
| 3 | (THP ring) (=THP) |
| 4 | —CH$_2$OCH$_3$ (=MOM) |
| 5 | —Si(CH$_3$)$_2$C$_4$H$_9^t$ (=TBS) |
| 6 | —C(=O)CH$_3$ (=AC) |
| 7 | —C(=O)C$_6$H$_5$ (=Bz) |

| Compound No. | $R^2$ |
|---|---|
| 15 | —H |
| 16 | —EE |
| 17 | —THP |
| 18 | —MOM |
| 19 | —TBS |
| 20 | —AC |
| 21 | —Bz |

(4) When $R^1$ is:

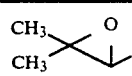

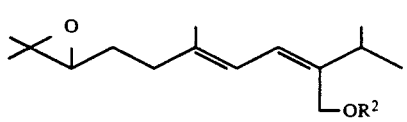

| Compound No. | $R^3$ | $R^4$ | $R^2$ |
|---|---|---|---|
| 22 | —CH$_3$ | —CH$_3$ | —H |
| 23 | —CH$_3$ | —CH$_3$ | —EE |
| 24 | —CH$_3$ | —CH$_3$ | —THP |
| 25 | —CH$_3$ | —CH$_3$ | —MOM |
| 26 | —CH$_3$ | —CH$_3$ | —TBS |
| 27 | —CH$_3$ | —CH$_3$ | —AC |
| 28 | —CH$_3$ | —CH$_3$ | —Bz |
| 29 | —CH$_2$CH$_3$ | —CH$_2$CH$_3$ | —EE |
| 30 | —CH$_2$CH$_3$ | —CH$_2$CH$_3$ | —TBS |
| 31 | —CH$_2$CH$_2$CH$_2$CH$_2$— | | —TBS |
| 32 | —CH$_2$CH$_2$CH$_2$CH$_2$CH$_2$— | | —TBS |

(2) When $R^1$ is:

| Compound No. | $R^2$ |
|---|---|
| 8 | —H |
| 9 | —EE |
| 10 | —THP |
| 11 | —MOM |
| 12 | —TBS |
| 13 | —AC |
| 14 | —Bz |

(5) When $R^1$ is:

| Compound No. | $R^3$ | $R^4$ | $R^2$ |
|---|---|---|---|
| 33 | —CH$_3$ | —CH$_3$ | —H |
| 34 | —CH$_3$ | —CH$_3$ | —EE |
| 35 | —CH$_3$ | —CH$_3$ | —THP |
| 36 | —CH$_3$ | —CH$_3$ | —MOM |
| 37 | —CH$_3$ | —CH$_3$ | —TBS |
| 38 | —CH$_3$ | —CH$_3$ | —AC |
| 39 | —CH$_3$ | —CH$_3$ | —Bz |
| 40 | —CH$_2$CH$_3$ | —CH$_2$CH$_3$ | —EE |
| 41 | —CH$_2$CH$_3$ | —CH$_2$CH$_3$ | —TBS |
| 42 | —CH$_2$CH$_2$CH$_2$CH$_2$— | | —TBS |
| 43 | —CH$_2$CH$_2$CH$_2$CH$_2$CH$_2$— | | —TBS |

(3) When $R^1$ is:

(6) When $R^1$ is:

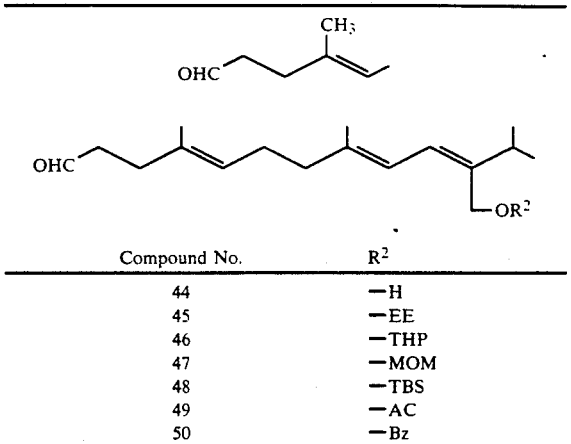

| Compound No. | $R^2$ |
|---|---|
| 44 | —H |
| 45 | —EE |
| 46 | —THP |
| 47 | —MOM |
| 48 | —TBS |
| 49 | —AC |
| 50 | —Bz |

(7) When $R^1$ is:

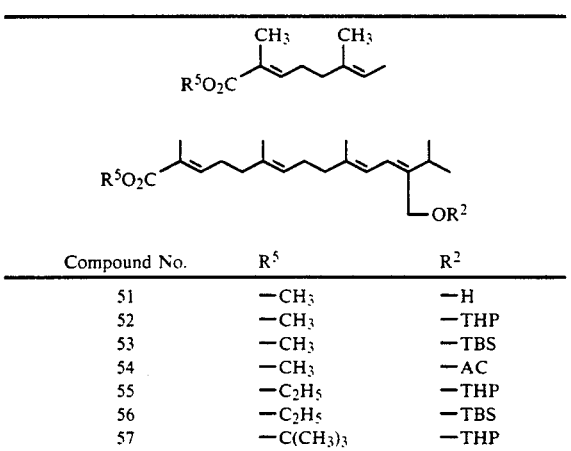

| Compound No. | $R^5$ | $R^2$ |
|---|---|---|
| 51 | —CH$_3$ | —H |
| 52 | —CH$_3$ | —THP |
| 53 | —CH$_3$ | —TBS |
| 54 | —CH$_3$ | —AC |
| 55 | —C$_2$H$_5$ | —THP |
| 56 | —C$_2$H$_5$ | —TBS |
| 57 | —C(CH$_3$)$_3$ | —THP |

(8) When $R^1$ is:

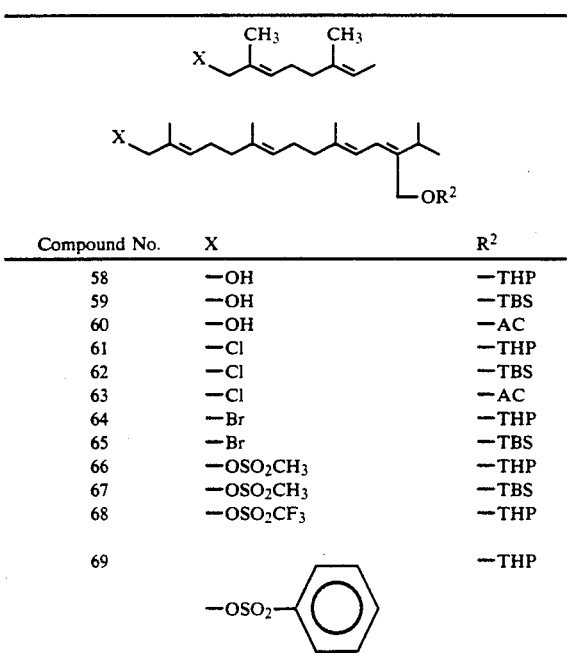

| Compound No. | X | $R^2$ |
|---|---|---|
| 58 | —OH | —THP |
| 59 | —OH | —TBS |
| 60 | —OH | —AC |
| 61 | —Cl | —THP |
| 62 | —Cl | —TBS |
| 63 | —Cl | —AC |
| 64 | —Br | —THP |
| 65 | —Br | —TBS |
| 66 | —OSO$_2$CH$_3$ | —THP |
| 67 | —OSO$_2$CH$_3$ | —TBS |
| 68 | —OSO$_2$CF$_3$ | —THP |
| 69 | —OSO$_2$—⟨phenyl⟩ | —THP |

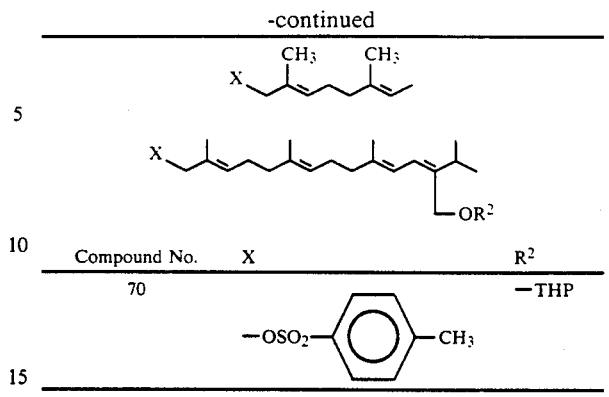

| Compound No. | X | $R^2$ |
|---|---|---|
| 70 | —OSO$_2$—⟨phenyl⟩—CH$_3$ | —THP |

The process for preparing the compounds (I) of the present invention will be explained below.

The compounds of the general formula (I) can be prepared, for example, according to the following synthetic route, starting from a monoterpenoid, geranial (K), available at low cost and in great quantities. In the following scheme, the compounds (I) are represented by (I)-(L)–(I)-(T).

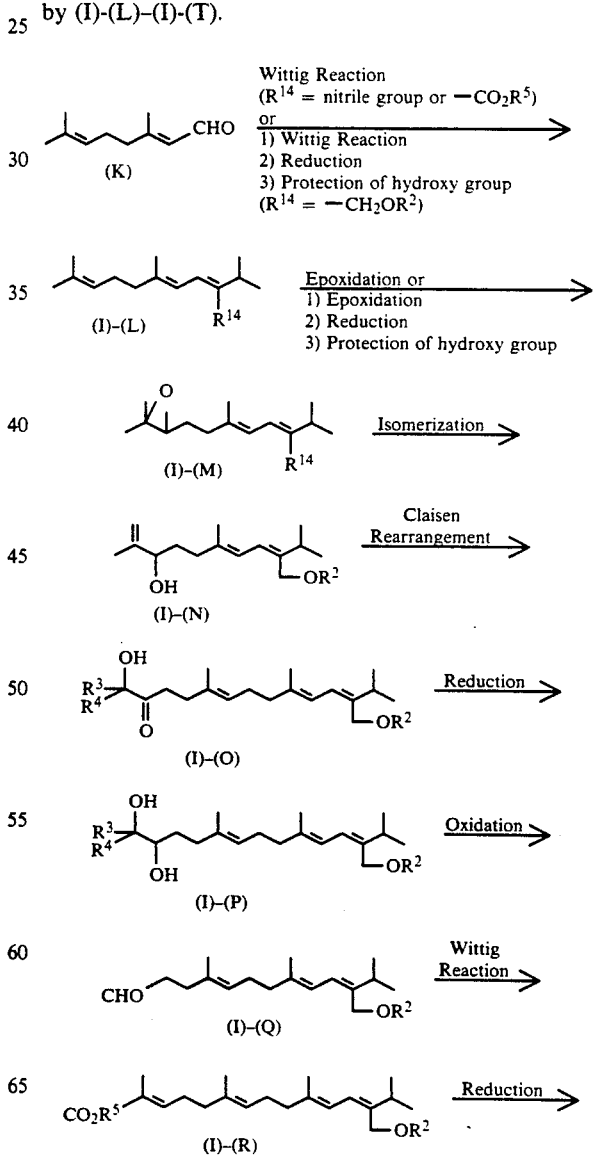

-continued

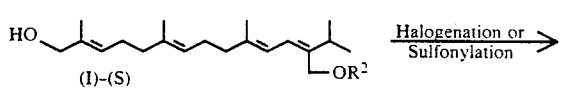

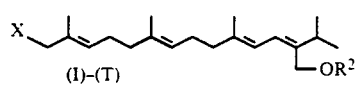

(in the above formulae, $R^{14}$ is $-CH_2OR^2$, nitrile group, formyl group, or $-CO_2R^5$, and $R^2$, $R^3$, $R^4$, $R^5$ and X have the same significance as defined above.)

(1) Preparation of the compound (I) wherein $R^1$ is

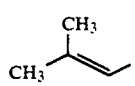

and $R^2$ is hydrogen:

For example, geranial (K) is allowed to react for 5 minutes to 24 hours with an anion derived from 0.1 to 10 equivalent of Wittig-Honer reagent such as ethyl 2-(diethylphosphono)isovalerate, 2-(dimethylphosphono)-isovaleronitrile or the like, said anion being generated by combining the reagent in an ethereal solvent such as tetrahydrofuran, diethyl ether or the like, a hydrocarbon solvent such as toluene, n-hexane or the like, an aprotic polar solvent such as dimethylformamide or the like, at temperature from $-100°$ C. to $+100°$ C. with not more than 1 equivalent of a base such as a metal hydride (e.g. sodium hydride, etc.), or an organic metal (e.g. n-butyllithium, lithium diisopropylamide, sodium methoxide, potassium t-butoxide, etc.), or geranial (K) is allowed to react with a phosphorane compound such as

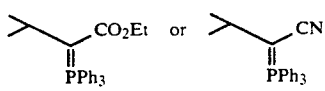

in a halogenated solvent such as methylene chloride, chloroform or the like, an ethereal solvent such as diethyl ether, tetrahydrofuran or the like, or an alcoholic solvent such as methanol, ethanol or the like, at temperature from $-50°$ C. to $+100°$ C. for 5 minutes to 24 hours to give the compound (I)-(L) in which $R^{14}$ is cyano group of $-CO_2R^5$ ($R^5$ =alkyl group of 1 to 4 carbon atoms). The product may be allowed to further react with 0.1 to 10 equivalent of a metal hydride such as diisobutylaluminum hydride or the like at temperature from $-100°$ C. to $+150°$ C. in a hydrocarbon solvent such as n-hexane, heptane, benzene or the like, followed by hydrolysis to give the compound (I)-(L) in which $R^{14}$ is formyl group. This compound may be further allowed to react with 0.1 to 10 equivalent of a metal hydride such as diisobutylaluminum hydride or the like in a hydrocarbon solvent such as n-hexane, toluene or the like, at temperature from $-100°$ C. to $+150°$ C. for 5 minutes to 24 hours, or with 0.1 to 10 equivalent of a metal hydride complex such as lithium aluminum hydride or the like in an ethereal solvent such as diethyl ether, tetrahydrofuran or the like, at temperature from $-100°$ C. to $+150°$ C. for 5 minutes to 24 hours, to give the compound (I) wherein $R^1$ is

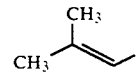

and $R^2$ is hydrogen atom.

(2) Preparation of the compound (K) wherein $R^1$ is

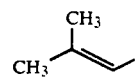

$R^2$ is

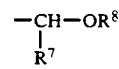

($R^7$ and $R^8$ are as defined above):

For example, this compound may be prepared by reacting the compound of the formula (I) (in which $R^1 =$

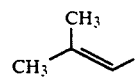

$R^2 =$ hydrogen atom), which is obtained by the process in the above process 1), with 0.1 to 10 equivalent of 1-haloalkylether such as chloromethyl methyl ether, chloromethyl-(2-methoxy)ethyl ether or the like, in a halogenated solvent such as methylene chloride, chloroform or the like, an ethereal solvent such as diethyl ether, tetrahydrofuran or the like, or an aprotic polar solvent such as ethyl acetate, dimethyl formamide or the like, or without solvent, in the presence of 0.1 to 10 equivalent of a metal hydride such as sodium hydride, potassium hydride or the like, an amine such as triethylamine, diisopropylethylamine or the like, or pyridine or the like, at temperature from $-20°$ C. to $+100°$ C. for 5 minutes to 24 hours. Alternatively, the above-noted compound of the formula (I) can be reacted with 0.1 to 10 equivalent of vinyl ether such as ethyl vinyl ether, dihydropyran or the like in the presence of a catalytic amount of a mineral acid such as hydrochloric acid, sulfuric acid or the like, an organic sulfonic acid such as p-toluenesulfonic acid, camphorsulfonic acid or the like, or a salt of strong acid such as p-toluenesulfonic acid pyridinium salt or the like, in a halogenated solvent such as dichloromethane, chloroform or the like, an ethereal solvent such as diethyl ether, tetrahydrofuran or the like, or ethyl acetate, diethylformamide or the like solvent, or without solvent, at temperature from $-20°$ C. to $+100°$ C. for 5 minutes to 24 hours.

(3) Preparation of the compound (I) in which $R^1$ is

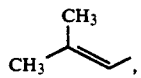

$R^2$ is

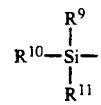

($R^9$ to $R^{11}$ are as defined above):

For example, this compound may be prepared by reacting the compound of the formula (I) (in which $R^1$ is

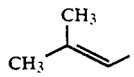

$R^2$ is hydrogen), which is obtained in the above process 1), with 0.1 to 10 equivalent of chlorosilane such as trimethylchlorosilane, dimethyl-t-butylchlorosilane or the like in a halogenated solvent such as methylene chloride, chloroform or the like, a hydrocarbon solvent such as hexane, benzene or the like, an ethereal solvent such as diethyl ether, tetrahydrofuran or the like, or an aprotic polar solvent such as ethyl acetate, dimethylformamide, diethyl sulfoxide or the like, in the presence of 0.1 to 10 equivalent of a nitrogen-containing compound such as triethylamine, dimethylaminopyridine, imidazole or the like, or a metal hydride such as sodium hydride, potassium hydride, at temperature from $-20°$ C. to $+100°$ C. for 5 minutes to 24 hours.

(4) Preparation of the compound (I) in which $R^1$ is

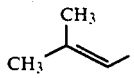

$R^2$ is acyl group:

This compound may be prepared, for example, by reacting the compound of the formula (I) (in which $R^1=$

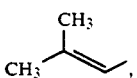

$R^2$=hydrogen atom), which is obtainable in the process 1), with 0.1 to 10 equivalent of an acyl halide such as acetyl chloride, benzoyl chloride or the like or an acid anhydride such as acetic anhydride or the like, in a halogenated solvent such as dichloromethane or the like, an ethereal solvent such as diethyl ether or the like, or a hydrocarbon solvent such as benzene, n-hexane or the like, or using a base such as 0.1 to 10 equivalent of triethylamine or pyridine as a solvent, at temperature from $0°$ C. to $+100°$ C. for 30 minutes to 24 hours.

(5) Preparation of the compound (I) in which $R^1$ is

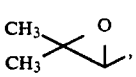

$R^2$ is hydrogen atom,

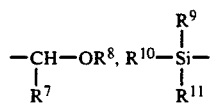

or acyl group, wherein $R^7$-$R^{11}$ are as defined above.

This compound may be prepared by epoxidation of the compound of the formula (I)

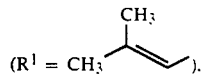

which is obtainable by the above process 1)-4), by reacting the compound with 0.1 to 10 equivalent of an organic peracid such as peracetic acid or m-chloroperbenzoic acid, in a halogenated solvent such as methylene chloride, chloroform or the like, an ester solvent such as ethyl acetate or the like, or an ethereal solvent such as tetrahydrofuran, ether or the like, at temperature from $-50°$ C. to $+100°$ C.; or by reacting the same with 0.1 to 10 equivalent of an N-halocarboxyamide such as N-bromosuccinimide, N-chlorosuccinimide, N-bromoacetamide or the like, in a solvent such as aqueous tetrahydrofuran, aqueous dioxane or the like, at temperature from $-20°$ C. to $+100°$ C. for 5 minutes to 5 hours and subsequently reacting the resultant product with a base such as sodium carbonate, potassium carbonate or the like, or by reacting the same with hydrogen peroxide in nitrile such as acetonitrile, benzonitrile or the like. Alternately, the compound (I) wherein $R^1$ is

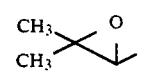

and $R^2$ is hydrogen may be prepared by reacting the compound (I)-(M) (in which $R^{14}$ is CN group), which is obtainable by subjecting the intermediate (I)-(L) (in which $R^{14}$ is as defined above) t epoxidation as described above, with 0.1 to 10 equivalent of a metal hydride such as diisobutylaluminum hydride or the like at temperature from $-100°$ C. to $+150°$ C. for 5 minutes to 12 hours, followed by hydrolysis to give the compound (I)-(M) (in which $R^{14}$ i —CHO group), and reacting the resulting product with 0.1 to 10 equivalent of a metal hydride such as diisobutylaluminum hydride or the like, at temperature from $-100°$ C. to $+150°$ C. for 5 minutes to 24 hours, with 0.1 to 10 equivalent of a hydride complex such as sodium borohydride or the like in an alcoholic solvent such as methanol, ethanol or the like, at temperature from $-100°$ C. to $+150°$ C. for 5 minutes to 24 hours. Further or the compound (I) (in which $R^1=$

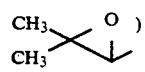

may be prepared from the above product in accordance with the previously-mentioned process (2)-(4).

(6) Preparation of the compound (I) in which $R^1$ is

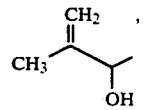

and $R^2$ is as defined in the above process 5):

This compound is prepared, for example, by reacting the compound of the formula (I) (in which $R^1=$

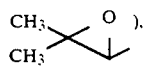

which is obtainable by the above process 5), with 0.1 to 10 equivalent of an aluminum alkoxide such as aluminum isopropoxide or the like, in a hydrocarbon solvent such as toluene, xylene, ligroin or the like, at temperature from 0° C. to 150° C. for 5 minutes to 24 hours, or by reacting the same compound with 0.1 to 10 equivalent of a metal amide such as lithium diethylamide, lithium diisopropylamide or the like, in a solvent such as diethyl ether, tetrahydrofuran or the like, at temperature rom −100° C. to +100° C.

(7) Preparation of the compound of the formula (I) wherein

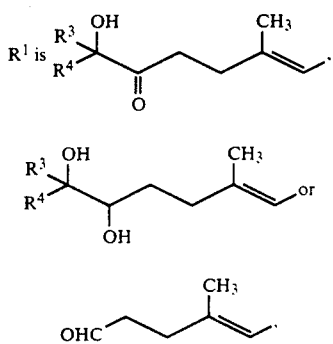

R² is

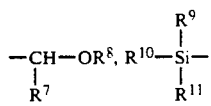

or acyl group (R³, R⁴ and R⁷-R¹¹ are as defined above):

This compound may be prepared by reacting the allyl alcohol (I) in which R¹ is

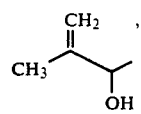

R² is

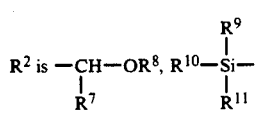

or acyl group, which is obtainable from the above process 6), with 0.1 to 50 equivalent of 3,3-dimethoxy-2-methylbutanol without solvent or in a solvent such as toluene, xylene, quinoline or the like, in the presence of 0.01 to 5 equivalent of 2,4-dinitrophenol, oxalic acid, 0-nitro-benzoic acid or the like acid, while distilling off the generated methanol at temperature from 100 C. to 250° C. for 5 minutes to 12 hours. This reaction, called Claisen rearrangement, gives the compound (I) wherein R¹ is

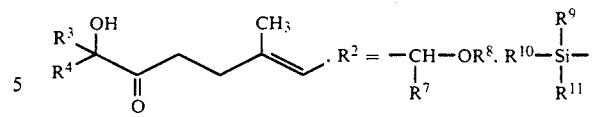

or acyl group (R³, R⁴ and R⁷-R¹¹ are as defined above). The product is then allowed to react with 0.1 to 10 equivalent of a reducing agent such as sodium borohydride, sodium cyanoborohydride or the like, in a solvent such as methanol, ethanol or the like, at temperature from −80° C. to +100° C. for 5 minutes to 24 hours to give the compound (I) wherein R¹ is

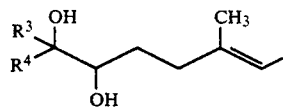

and R² is as defined above. This compound is allowed to react with 0.1 to 10 equivalent of a periodic acid salt such as sodium methaperiodate in an alcoholic solvent such as methanol, ethanol, aqueous methanol or the like, at temperature from −50° C. to +100° C. for 5 minutes to 5 days to give the compound (I) wherein R¹ is

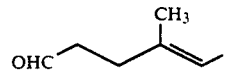

and R² is as defined above. Further, in order to obtain the title compound, the compound (I) wherein R¹=

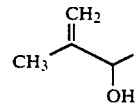

and R² is as defined above may be allowed to react with 1 to 100 equivalent of an alkyl vinyl ether such as ethyl vinyl ether or the like, in the presence of 0.1 to 5 equivalent of a mercury salt such as mercury acetate or the like, at temperature from 0° C. to 100° C. to give a vinyl ether derivative of the compound (I) wherein R¹ is

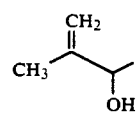

and R² is as defined above. Alternatively, the compound (I) wherein R¹ is

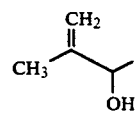

and R² is as defined above may also be converted into 3-alkoxyacrylic acid in accordance with the disclosure of J. Org. Chem., 48, 5406 (1983). The resultant product obtained above may be heated with a catalytic amount of hydroquinone or the like at +100° C. to +250° C. to yield the objective product.

(8) Preparation of the compound (I) in which R¹ is

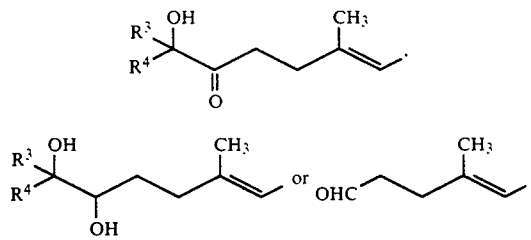

and $R^2$ is hydrogen atom (wherein $R^3$ and $R^4$ are as defined above):

This compound is prepared, for example, by reacting the compound (I) in which $R^1$ is

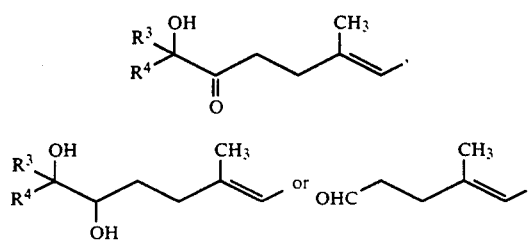

$R^2$ is

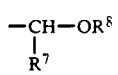

(wherein $R^3$, $R^4$, $R^7$ and $R^8$ are as defined above), with 0.1 to 10 equivalent of a mineral acid such as hydrochloric acid, sulfuric acid or the like, an organic strong acid such as p-toluenesulfonic acid or the like or a strong acid salt such as pyridinium p-toluenesulfonate or the like, in methanol, ethanol, aqueous tetrahydrofuran or their mixture, at temperature from $-10°$ C. to $+100°$ C. for 5 minutes to 24 hours, or by reacting the compound (I) in which $R^1$ is

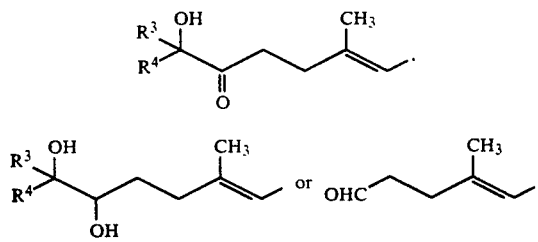

$R^2$ is

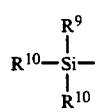

(wherein $R^3$, $R^4$, $R^9$-$R^{11}$ are as defined above), which is obtainable by the above process 7), with a tetraalkylammonium fluoride such as tetrabutylammonium fluoride or the like or a fluoric acid salt such as potassium fluoride or the like, in an ethereal solvent such as diethyl ether, tetrahydrofuran or the lie, an alcoholic solvent such as methanol, ethanol or the like, ethyl acetate, dimethylformamide or the like solvent, at temperature from $-10°$ C. to $+100°$ C. for 5 minutes to 24 hours; or by hydrolyzing the compound (I) in which $R^1$ is

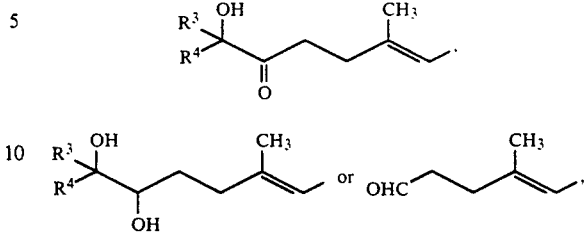

$R^2$ is acyl group (wherein $R^3$ and $R^4$ are as defined above), which is obtainable by the above process 7), with a base such as sodium hydroxide, potassium carbonate or the like, in aqueous methanol, aqueous ethanol, aqueous tetrahydrofuran or mixture thereof, at temperature from $-10°$ C. to $+100°$ C. for 5 minutes to 24 hours.

(9) Preparation of the compound (I) in which $R^1$ is

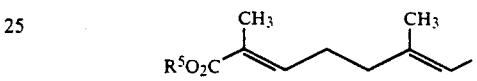

and $R^2$ is as defined in the preceding process 5) ($R^5$ is as defined above):

This compound is prepared by reacting the compound (I) in which $R^1$ is

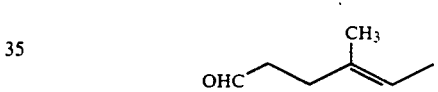

and $R^2$ is as defined in the preceding process 5), which is obtainable by the above process 7) or 8), with 0.1 to 5 equivalent of a phosphorane such as carbomethoxyethylidene triphenylphosphorane (where $R^5$ is methyl group), carboethoxyethylidene triphenylphosphorane (where $R^5$ is ethyl group) in a halogenated solvent such as chloroform, methylene chloride or the like, an ethereal solvent such as diethyl ether, tetrahydrofuran or the like, or an alcohol solvent such as methanol, ethanol or the like, at temperature from $-50°$ C. to $+100°$ C. for 5 minutes to 24 hours, or by reacting the above-noted compound (I) with an anion obtained by treating 2-(dialkylphosphono)-propionic acid ester such as ethyl 2-(diethylphosphono)-propionate (where $R^5$ is ethyl group) or the like with a base such as sodium hydride, n-butyllithium, lithiumdiisopropylamide, sodium methoxide or the like, in an ethereal solvent such as diethyl ether, tetrahydrofuran or the like, an aprotic polar solvent such as dimethylformamide, dimethylsulfoxide or the like or an alcoholic solvent such as methanol, ethanol, t-butyl alcohol or the like, at temperature from $-100°$ C. to $+100°$ C. for 5 minutes to 24 hours.

(10) Preparation of the compound (I) in which $R^1$ is

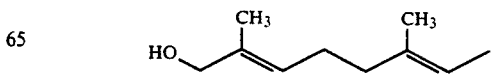

$R^2$ is H,

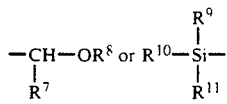

($R^7$-$R^{11}$ are as defined above):

This compound may be prepared, for example, by reacting the compound (I) in which $R^1$ is

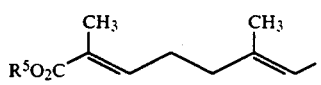

($R^5$ is as defined above), which is obtainable by the above process 9), with 0.1 to 10 equivalent of a metal hydride such as diisopropylaluminum hydride or the like, at temperature from $-100°$ C. to $+100°$ C. for 5 minutes to 24 hours, or by reacting the above-noted compound (I) with 0.1 to 10 equivalent of a metal hydride complex such as aluminum hydride in an ethereal solvent such as diethyl ether, tetrahydrofuran or the like, at temperature from $-100°$ C. to $+100°$ C. for 5 minutes to 24 hours.

(11) Preparation of the compound (I) in which $R^1$ is

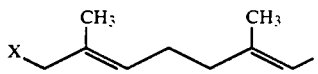

and X is halogen atom or —$OSO_2R^6$ ($R^6$ is as defined above), $R^2$ is

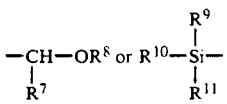

($R^7$-$R^{11}$ are as defined above):

This compound may be prepared by halogenating the compound (I) in which $R^1$ is

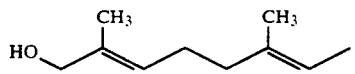

and $R^2$ is

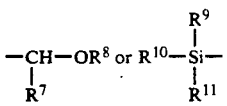

($R^7$-$R^{11}$ are as defined above), which is obtainable by the process 10) without causing allyl rearrangement of the allyl alcohol moiety. For example, the above compound (I) is reacted with 1 to 10 equivalent of a carbon tetrahalide in the presence of 1 to 10 equivalent of triphenylphosphine in an inert solvent such as acetonitrile, methylene chloride or the like, at temperature from 0° C. to 100° C. for 0.5 to 12 hours (carbontetrachloride may be used as a chlorinating agent and also as a solvent therefor), or by reacting the compound (I) with 1 to 10 equivalent of methanesulfonyl chloride, a metal halide and s-collidine in an aprotic polar solvent such as dimethylformamide or the like, at temperature from $-40°$ C. to room temperature for 1 to 10 hours. Further, the compound wherein X is —$OSO_2R^6$ can be prepared by reacting the starting alcohol with 1 to 10 equivalent of a sulfonic acid chloride such as methanesulfonyl chloride, p-toluenesulfonyl chloride or the like, or a sulfonic acid anhydride such as trifluoromethanesulfonic anhydride or the like, in the presence of 1 to 10 equivalent of an amine such as triethylamine, pyridine or the like, in an ethereal solvent such as ethyl ether, tetrahydrofuran or the like, or a halogenated solvent such as methylene chloride, chloroform or the like, at temperature from $-40°$ C. to room temperature for 1 to 10 hours. In this reaction, pyridine may be used as a base and also a solvent at the same time.

(12) Preparation of the compound (I) in which $R^1$ is

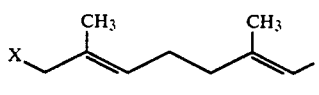

and $R^2$ is acyl group (X is as defined above):

This compound may be prepared, for example, by reacting the compound (I) wherein $R^1$ is

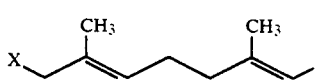

(X is as defined above), $R^2$ is

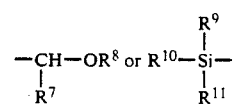

($R^7$-$R^{11}$ are as defined above), which is obtainable by the above process 11), with 0.1 to 10 equivalent of a mineral acid such as hydrochloric acid, sulfuric acid or the like, an organic strong acid such as p-toluenesulfonic acid or the like, or a strong acid salt such as pyridinium p-toluenesulfonic acid or the like, in a solvent such as methanol, ethanol, aqueous tetrahydrofuran or mixture thereof, at temperature from $-10°$ C. to $+100°$ C. for 5 minutes to 24 hours, or by reacting the compound (I) with tetraalkylammonium fluoride such as tetrabutylammonium fluoride or the like, or hydrofluoric acid salt such as potassium fluoride or the like, in an ethereal solvent such as tetrahydrofuran or the like, an alcoholic solvent such as methanol, ethanol or the like, ethyl acetate, dimethylformamide or the like solvent, at temperature from $-10°$ C. to $+100°$ C. for 5 minutes to 24 hours to give the compound (I) in which $R^1$ is

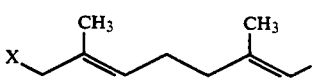

and $R^2$ is hydrogen atom, followed by acylation according to the above process 4).

According to the present invention, the key intermediate (E) in the Synthetic Route 1 of sarcophytol A is easily prepared starting from monoterpenoids, which are available at low cost and in great quantities, through the compounds (I) of the present invention without necessity of the hazardous oxidation step (C) of the terminal methyl group, as previously mentioned.

For instance, Compound (E) can be prepared by reacting the compound of the general formula (I) in which R¹ is

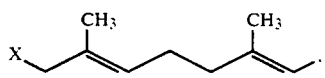

and R² is

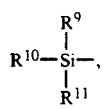

and $R^9$-$R^{11}$ are as defined above, with a tetraalkylammonium fluoride such as tetrabutylammonium fluoride or the like, or a fluoric acid salt such as potassium fluoride or the like, in an ethereal solvent such as ether, tetrahydrofuran or the like, an alcoholic solvent such as methanol, ethanol or the like, or an aprotic polar solvent such as ethyl acetate, dimethylformamide or the like, at temperature from −10° C. to +100° C. for 5 minutes to 24 hours. Compound (E) thus obtained can be converted into sarcophytol A according to the synthetic route described in Japanese Patent Application No. 181710/1989.

Briefly, Compound (F) in said route can be prepared by reacting Compound (E) prepared above with 5 to 20 fold by weight of an oxidizing agent such as powdery manganese dioxide, barium manganate or the like in a halogenated solvent such as methylene chloride, chloroform or the like, a hydrocarbon solvent such as hexane, heptane or the like, ethyl ether, ethyl acetate or the like, at temperature from 0° C. to 50° C. for 1 to 50 hours.

Compound (G) (in which $R^{13}$ is trimethylsilyl group) in said route can be prepared, for example, by reacting Compound (F) prepared above with 1 to 10 equivalent of trimethylsilyl nitrile in the presence of a catalytic amount of metal-18-crown-6-ether cyanide complex in a solvent such as methylene chloride, chloroform, ethyl acetate or the like or without solvent, at temperature from −20° C. to +50° C. for 30 minutes to 5 hours. Cyanohydrin compound (G) (in which $R^{13}$ is hydrogen atom) can be prepared by reacting the compound (G) in which $R^{13}$ is trimethylsilyl with 0.1 to 3N aqueous mineral acid such as hydrochloric acid, sulfuric acid or the like, in a solvent such as tetrahydrofuran, methanol or the like, at temperature from 0° C. to room temperature for 5 minutes to 5 hours, or by reacting the same compound with 10 equivalent of tetraalkylammonium fluoride such as tetrabutylammonium fluoride or the like, in a solvent such as tetrahydrofuran, dioxane or the like, at temperature from −20° C. to room temperature.

Further, Compound (G) (in which $R^{13}$ is 1-ethoxyethyl group) can be prepared by reacting the above-noted cyanohydrin with 1 to 10 equivalent of ethyl vinyl ether in the presence of a catalytic amount of a mineral acid such as hydrochloric acid, sulfuric acid or the like, an organic strong acid such as p-toluenesulfonic acid or the like, or a strong acid salt such as pyridinium p-toluenesulfonate or the like, at temperature from −20° C. to room temperature for 30 minutes to 5 hours.

Compound (H) (in which $R^{13}$ is trimethylsilyl group or 1-ethoxyethyl group) may be prepared by reacting Compound (G) in which $R^{13}$ is trimethylsilyl group or 1-ethoxyethyl group) with 1 to 10 equivalent of a base such as lithium diisopropylamide, lithiumbis-(trimethylsilyl)amide, sodium hydride or the like in an ethereal solvent such as ethyl ether, tetrahydrofuran or the like, an aromatic hydrocarbon solvent such as benzene, toluene or the like, or a saturated hydrocarbon solvent such as n-hexane, n-heptane or the like, at temperature from −70° C. to +100° C. for 5 minutes to 10 hours. Further, Compound (H) (in which $R^{13}$ is hydrogen atom) can be prepared by reacting the resulting Compound (H) in which $R^{13}$ is trimethylsilyl or 1-ethoxyethyl group, with 0.1 to 3N aqueous mineral acid such as hydrochloric acid, sulfuric acid or the like, in a solvent such as tetrahydrofuran, methanol or the like, at temperature from 0° C. to room temperature for 5 minutes to 5 hours, or by reacting the starting Compound (H) with a catalytic amount to 10 equivalent of a tetraalkylammonium compound such as tetrabutylammonium fluoride or the like, in a solvent such as tetrahydrofuran, dioxane or the like, at temperature from −20° C. to room temperature.

Ketone compound (J) can be prepared by reacting the compound (H) (in which $R^{13}$ is hydrogen atom) with aqueous sodium bicarbonate in an organic solvent such as ethyl ether, ethyl acetate or the like, at temperature from 0° C. to room temperature for 5 minutes to 5 hours, or by reacting the compound (H) (in which $R^{13}$ is trimethylsilyl group) with a catalytic amount to 10 equivalent of alkylammonium fluoride such as tetrabutylammonium fluoride in a solvent such as aqueous tetrahydrofuran, dioxane or the like. The resulting compound (J) is allowed to react with 1 to 10 equivalent of a metal hydride such as dibutylaluminum hydride or the like or a metal complex such as lithium aluminum hydride or the like in an ethereal solvent such as ethyl ether, tetrahydrofuran or the like, an aromatic hydrocarbon solvent such as benzene, toluene or the like, or a saturated hydrocarbon solvent such as n-hexane, n-heptane or the like, at temperature from −70° C. to +50° C. for 5 minutes to 5 hours to give sarcophytol A.

As will be understood from the above, the present invention provides industrially advantageous means for preparing sarcophytol A.

Presently preferred and practical embodiments of the present invention are illustratively shown in the following examples, but these examples should not be construed as limiting the present invention in any respect.

Preparation 1

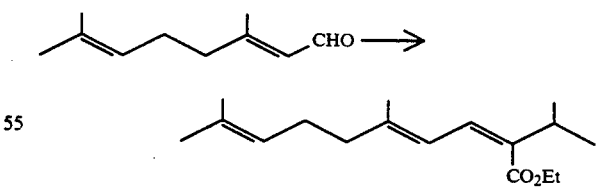

To a solution of ethyl 2-(dimethylphosphono)-3-methylbutyrate (11.0 g, 41.3 mmol) in tetrahydrofuran (50 ml) chilled at −68° C. was dropwise added 1.62M solution of n-butyllithium in hexane (21.6 ml, 35.0 mmol) with stirring in 15 minutes under argon atmosphere. After stirring at −72° C. for 15 minutes, the mixture was mixed with geranial (4.0 g, 26.3 mmol), warmed up to room temperature in 30 minutes and stirred for 5 hours. The reaction mixture was chilled on an ice bath and mixed with saturated aqueous ammonium chloride (100 ml) and hexane (100 ml). The organic layer was separated, washed with saturated aqueous sodium chloride (50 ml), dried over anhydrous sodium sulfate, and concentrated under reduced pressure to remove the solvent. The resulting residue was chromatographed on a silica gel column (Eluent: n-hexane:ether=30:1) to give ethyl 2-(1-methylethyl)-5,9-dimethyl-2,4,8-decatrienate (3,07 g, 48%).

$^1$HNMR (CDCl$_3$, 250 MHz) δ ppm: 1.10 (d, J=6.9 Hz, 6H, (CH$_3$)$_2$CH—), 1.34 (t, J=7.0 Hz, 3H, OCH$_2$CH$_3$), 1.60, 1.68, 1.82 (3s, 9H, (CH$_3$)$_2$C=CH—, CH$_3$C=CH—), 2.80 (hep, J=6.9 Hz, 1H, (CH$_3$)$_2$CH—), 4.26 (q, J=7.0 Hz, 2H, —OCH$_2$CH$_3$), 5.12 (m, 1H, (CH$_3$)$_2$C=CH—), 6.56 (s, 2H, —C=CH—CH—CO$_2$Et).

Preparation 2

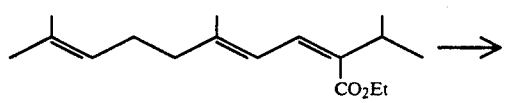

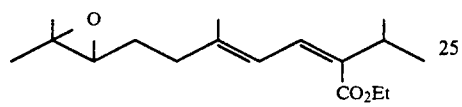

A solution of ethyl 2-(1-methylethyl)-5,9-dimethyl-,2,4,8-decatrienate (300 mg, 1.22 mmol) in dichloromethane (4 ml) was stirred on an ice bath and mixed portionwise with sodium bicarbonate (200 mg, 2.38 mmol) and m-chloroperbenzoic acid (Purity 80% 290 mg, 1.34 mmol). The mixture was stirred on an ice bath for 15 minutes, mixed with aqueous saturated sodium bicarbonate (10 ml), n-hexane (10 ml) and ether (20 ml), and vigorously stirred. Insoluble material was filtered off, and the filtrate was extracted with ether several times. The extract was dried over anhydrous sodium sulfate, and concentrated. The resulting residue was chromatographed on a silica gel column (Eluent: n-hexane:ether=10:1) to give the objective epoxy compound (253 mg, 79%).

IR (film) cm$^{-1}$; 2960, 2930, 2870, 1708, 1630, 1460, 1378, 1305, 1230, 1195, 1148, 1038, 882, 785.

$^1$HNMR (CDCl$_3$, 250 MHz) δ ppm: 1.45 (d, J=18.9 Hz, 6H, (CH$_3$)$_2$CH—), 1.36, 1.30 (each s, each 3H, OC(CH$_3$)$_2$), 1.33 (t, J=7.2 Hz, 3H, OCH$_2$CH$_3$), 1.62–1.75 (m, 2H, C=C—CH$_2$— CH$_2$—), 1.84 (s, 3H, CH$_3$C=C—), 2.14–2.38 (m, 2H, C=C—CH$_2$—CH$_2$—), 2.72 (t, J=6.2 Hz, 1H, —CHO—), 2.80 (hep, J=6.8 Hz, 1H, —CH(CH$_3$)$_2$), 4.25 (q, J=7.2 Hz, 2H, OCH$_2$CH$_3$), 6.53 (d, J=11.5 Hz, 1H, =CH—CH=), 6.60 (dd, J=11.5, 1.1 Hz, 1H, =CH—CH=).

EXAMPLE 1

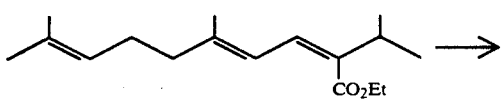

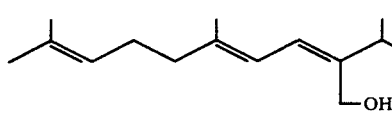

To a solution of ethyl 2-(1-methylethyl)-5,9-dimethyl-2,4,8-decatrienate (280 mg, 1.14 mmol) in toluene (5 ml) chilled at −72° C. under argon atmosphere was dropwise added 0.92M solution of diisobutylaluminum hydride in hexane (3.72 ml, 3.42 mmol). After stirring at −72° C. for 10 minutes, the reaction mixture was mixed with water (1.5 ml) for stopping the reaction. The reaction mixture was vigorously stirred at room temperature for 1 hour, and precipitates were filtered off. The filtrate was concentrated and the residue was chromatographed on a silica gel column to give 2-(1-methylethyl)-5,9-dimethyl-2,4,8-decatrien-1-ol (214 mg, 84%).

IR (film) cm$^{-1}$; 3330, 2960, 2925, 2870, 1440, 1375, 1008.

$^1$HNMR (CDCl$_3$+D$_2$O, 250 MHz) δ ppm; 1.09 (d, J=6.8 Hz, 6H, (CH$_3$)$_2$CH—), 1.61, 1.69, 1.78 (each s, each 3H, (CH$_3$)$_2$C=, CH$_3$—C=), 2.00–2.18 (m, 8H, =CH—CH$_2$—CH$_2$—), 2.49 (hep, J=6.8 Hz, 1H, (CH$_3$)$_2$ CH—), 4.25 (s, 2H, —CH$_2$OH), 5.10 (m, 1H, C=CH—CH$_2$—), 6.10–6.20 (m, 2H, =CH—CH=).

EXAMPLE 2

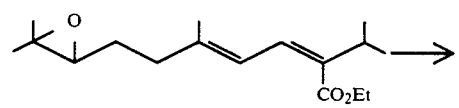

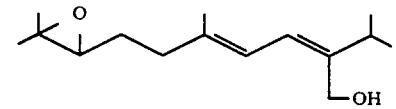

To a solution of the epoxy-ester compound shown above (3.63 mg, 1.38 mmol), which was dissolved in toluene (10 ml) and chilled at −74° C. under argon atmosphere, was dropwise added 0.92M solution of diisobutylaluminum hydride in hexane (3.00 ml, 2.76 mmol). After stirring at this temperature for 10 minutes, the mixture was mixed with water (2 ml) and stirred at room temperature for 30 minutes. Resultant precipitates were filtered, and the filtrate was concentrated to give crude epoxy-alcohol compound, which was chromatographed on a silica gel column (Eluent: n-hexane:ether=5:1) to give the objective product (290 mg, 88%).

IR (film) cm$^{-1}$; 3450, 2960, 2930, 2870, 1460, 1377, 1120, 1050.

$^1$HNMR (CDCl$_3$+D$_2$O, 250 MHz) δ ppm; 1.09 (d, J=6.9 Hz, 6H, (CH$_3$)$_2$CH—), 1.27, 1.31 (each s, each 3H, (CH$_3$)$_2$CO—), 1.68 (q, J=7.2 Hz, 2H, =C—CH$_2$—CH$_2$—), 2.25 (ddd, J=7.2, 14.1, 29.2 Hz, 2H, =C—CH$_2$—CH$_2$—), 2.50 (hep, J=6.9 Hz, 1H, (CH$_3$)$_2$CH—), 2.73 (t, J=6.8 Hz, 1H, CHO—), 4.25 (s, 2H, CH$_2$OH), 6.17, 6.21 (each d, J=11.6 Hz, each 1H, =CH—CH=).

EXAMPLE 3

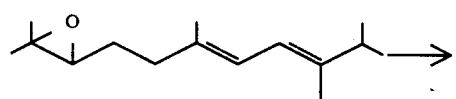

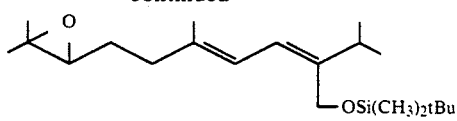
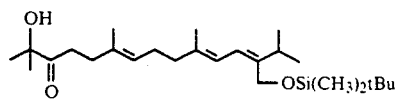

[in which tBu means [C(CH$_3$)$_3$]]]

To a solution of the epoxy-alcohol compound shown above (112 mg, 0.47 mmol), which was dissolved in dimethylformamide (3 ml), were added imidazole (64 mg, 0.94 mmol) and dimethyl-t-butylchlorosilane (93 mg, 0.62 mmol), and the resultant mixture was stirred at room temperature for 30 minutes. Saturated brine (5 ml) was added to the mixture, and reaction product was shaken with n-hexane (20 ml×2). The extract was dried over anhydrous sodium sulfate, concentrated, and the residue was chromatographed on a silica gel column to give the silyl ether compound (166 mg, quantitatively).

IR (film) cm$^{-1}$; 2975, 2945, 2870, 1460, 1380, 1260, 1080, 835, 775.

$^1$HNMR (CDCl$_3$, 250 MHZ) δ ppm; 0.08 (s, 6H, (CH$_3$)$_2$Si), 0.90 (s, 9H, (CH$_3$)$_3$C), 1.07 (d. J=6.9 Hz, 6H, (CH$_3$)$_2$CH—), 1.26, 1.31 (each s, each 3H, (C$\overline{\text{H}}_3$)$_2$CO—), 1.60–1.75 (m, 2H, =C—CH$_2$—CH$_2$—), 2.08–2.36 (m, 2H, =C—CH$_2$—CH$_2$—), 2.54 hep, $\overline{\text{J}}$=6.9 Hz, 1H, (CH$_3$)$_2$ CH—), 2.73 (t, J=6.2 Hz, 1H, CHO—), 4.29 (s, 2H, CH$_2$OSi), 6.08, 6.05 (each d, J=11.4 Hz, each 1H, =CH—CH=).

EXAMPLE 4

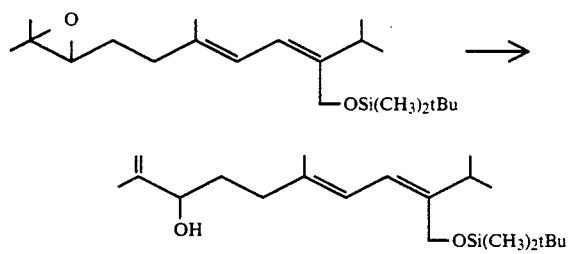

To a solution of the epoxy-silyl ether compound shown above (138 mg, 0.39 mmol), which was dissolved in toluene, was added aluminum isopropoxide (102 mg, 0.50 mmol), and the resultant mixture was refluxed for 4 hours. The reaction mixture was mixed with n-hexane (30 ml) and washed with dilute hydrochloric acid (10 ml), saturated aqueous sodium bicarbonate (20 ml) and saturated brine (20 ml) in this order. The organic layer was dried over anhydrous magnesium sulfate and concentrated under reduced pressure to give the allyl alcohol compound (138 mg, quantitatively).

IR (film) cm$^{-1}$; 3380, 2970, 2940, 2860, 1250, 1080, 1060, 835, 773.

$^1$HNMR (CDCl$_3$+D$_2$O, 250 MHz) δ ppm; 0.08 (s, 6H, (CH$_3$)$_2$ Si), 0.91 (s, 9H, (CH$_3$)$_3$C), 1.07 d, J=6.8 Hz, 6H, (C H$_3$)$_2$CH, 1.60–1.80 (m, 2H, =C—CH$_2$—CH$_2$—), 1.73, 1.77 (each s, each 3H, CH$_3$C=x2), 4.06 (t, J=6.3 Hz, 1H, CHOH), 4.23 (s, 2H, CH$_2$OSi), 4.86, 4.96 (each brs, each 1H, H$_2$C=C), 6.05–6.20 (m, 2H, =C—CH=).

EXAMPLE 5

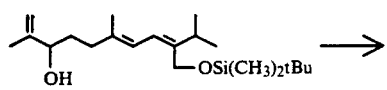

To a mixture of the allyl alcohol compound shown above (138 mg, 0.39 mmol) and 3,3-dimethoxy-2-methyl-2-butanol (290 mg, 1.96 mmol) was added 2,4-dinitrophenol (7.2 mg, 0.04 mmol), and the resultant mixture was heated at 150° C. on an oil bath under argon atmosphere for 1.5 hours. After allowing the mixture to be cooled, the excessive reagent was evaporated under reduced pressure, and the residue was chromatographed on a silica gel column to give the objective α-hydroxyketone compound (160 mg, 94%).

IR (film) cm$^{-1}$; 3500, 2970, 2945, 2870, 1710, 1460, 1360, 1255, 1075, 835, 773.

$^1$HNMR (CDCl$_3$+D$_2$O, 250 MHz) δ ppm; 0.08 (s, 6H, (CH$_3$)$_2$Si), 0.91 (s, 9H, (CH$_3$)$_3$Si), 1.07 (d, J=6.9 Hz, 6H, (CH$_3$)$_2$CH), 1.38 (s, 6H, (CH$_3$)$_2$COH), 1.63, 1.76 (each s, each 3H, (CH$_3$C=C—), 2.10 (brs, 4H, C=C—CH$_2$—CH$_2$—C=C), 2.29 (t, J=7.6 Hz, 2H, (C(=O)—CH$_2$—CH$_2$—CH$_2$—C=C—), 2.53 (hep, J=6.9 Hz, 1H, (CH$_3$)$_2$CH—), 2.64 (t, J=7.6 Hz 2H, C(=O)—CH$_2$—), 4.30 (s, 2H, CH$_2$OSi), 5.12 (brs, 1H, —C=CH—CH$_2$—), 6.10 (Brs, 2H, —C=CH—CH=C—).

EXAMPLE 6

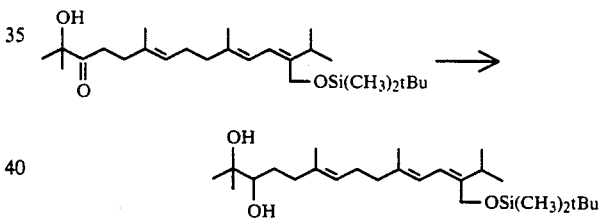

To a solution of the α-hydroxyketone compound shown above (153 mg, 0.35 mmol), which was dissolved in methanol (5 ml), was added sodium borohydride (13.3 mg, 0.35 mmol) on an ice bath with stirring, and the resultant mixture was stirred at the same temperature for 20 minutes. The mixture was mixed with saturated brine (20 ml), and the reaction product was extracted with ethyl acetate (20 ml×2). The extract was washed with saturated brine (20 ml), dried over anhydrous magnesium sulfate and the solvent was distilled off under reduced pressure. The residue was chromatographed on a silica gel column to give the objective diol compound (151 mg, 98%).

IR (film) cm$^{-1}$; 3420, 2960, 2940, 2870, 1462, 1380, 1360, 1252, 1870, 1060, 835, 773.

$^1$HNMR (CDCl$_3$+D$_2$O, 250 MHZ) δ ppm; 0.08 (s, 6H, (CH$_3$)$_2$Si), 0.91 (s, 9H, (CH$_3$)$_3$CSi), 1.07 (d, J=6.8 Hz, 6H, (CH$_3$)$_2$CH, 1.15, 1.19 ) (each s, each 3H, (CH$_3$)$_2$COH), 1.30–1.60 (m, 2H, —C—(OH)—CH$_2$—), 1.63, 1.76 (each s, each 3H, CH$_3$C=C—x2), 2.00–2.30 (m, 6H —CH$_2$—C(CH$_3$)=CH—CH$_2$—CH$_2$—), 2.53 hep J=6.8 Hz, 1H, (CH$_3$)$_2$ CH—), 3.34 (dd, $\overline{\text{J}}$=2.0, 10.4 Hz, 1H, —CHOH), 4.29 (s, 2$\overline{\text{H}}$, CH$_2$OSi), 6.10 6.05 (brs, 2H, —C=CH—CH=C—).

EXAMPLE 7

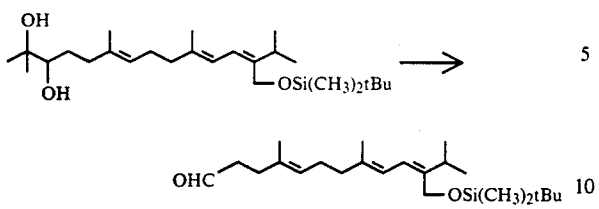

To a solution of the diol compound shown above (151 mg, 0.34 mmol), which was dissolved in methanol (4 ml)-water (0.6 ml), was added sodium metaperiodate (95 mg, 0.44 mmol), and the resultant mixture was stirred at room temperature overnight. Resultant precipitates were filtered off, and the filtrate was dissolved in diethyl ether-water, and the organic layer was washed with water, dried over anhydrous magnesium sulfate, and concentrated. The resultant residue was chromatographed on a silica gel column to give the objective aldehyde compound (120 mg, 94%).

IR (film) cm$^{-1}$; 2980, 2960, 2930, 2880, 2730, 1730, 1463, 1387, 1360, 1255, 1080, 1060, 840, 775, 670.

$^1$HNMR (CDCl$_3$, 250 MHZ) δ ppm; 0.08 (s, 6H, (CH$_3$)$_2$Si), 0.91 (s, 9H, (CH$_3$)$_3$Csi), 1.07 (d. J=6.8 Hz, 6H, (CH$_3$)$_2$CH—), 1.62, 1.75 (each s, each 3H, CH$_3$C=$\overline{\text{C}}$H—x2), 2.00–2.20 (m, 4H, =C—CH$_2$—CH$_2$—$\overline{\text{C}}$=), 2.32 (t, J=7.4 Hz, 2H, —CH$_2$—CH$_2$—CHO, 2.45–2.60 (m, 3H, —CH$_2$CHO, —C$\overline{\text{H}}$(CH$_3$)$_2$), 4.29 (s, 2H, CH$_2$OSi), 5.16 (m, 1H, —C=C$\overline{\text{H}}$—), 6.09 (s, 2H, —C=CH— CH=C—), 9.75 (t, $\overline{\text{J}}$=1.9 Hz, 1H, —CHO).

EXAMPLE 8

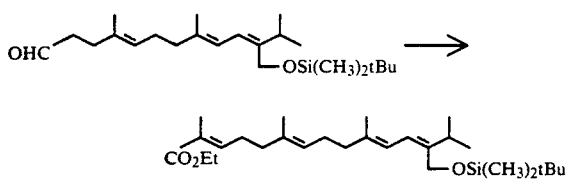

To a solution of the formyl compound shown above (110 mg, 0.29 mmol), which was dissolved in methylene chloride (6 ml), was added ethoxycarbonylethylidene triphenylphosphorane (Purity 98%, 148 mg, 0.40 mmol) on an ice bath with stirring, and the resultant mixture was stirred at the same temperature for 30 minutes. Then, it was warmed gradually up to room temperature, and stirred at room temperature for 7 hours. The mixture was mixed with saturated brine, and the reaction product was extracted with n-hexane. The extract was dried over anhydrous magnesium sulfate and concentrated, and the residue was chromatographed on a silica gel column to give the objective ester compound (130 mg, 97%).

IR (film) cm$^{-1}$; 2970, 2940, 2920, 2870, 1715, 1650, 1462, 1255, 1120, 1080, 1055, 835, 773.

$^1$HNMR (CDCl$_3$, 250 MHz) δ ppm: 0.08 (s, 6H, (CH$_3$)$_2$Si), 0.91 (s 9H, (CH$_3$)$_3$CSi), 1.07 (d, J=6.9 Hz, 6H, (CH$_3$)$_2$CH), 1.29 (t, J=7.1 Hz, 3H, —OCH$_2$CH$_3$), 1.62, 1.$\overline{76}$ (each s, each 3H, CH$_3$C=C—), 1.83 (d, J=1.1 Hz, 1H, CH$_3$—C=C—), 2.00–2.30 (m, 8H, —CH$_2$—CH$_2$—), 2.54 (hep, J=6.9 Hz, 1H, (CH$_3$)$_2$CH—), 4.18 (q, J=7.1 Hz, 2H, OCH$_2$CH$_3$), 4.30 (s, 2H, OCH$_2$Si), 5.17 (m, 1H, —C=C$\overline{\text{H}}$—CH$_2$—), 6.10 (brs, 1H, —C=CH— CH=C—), 6.74 (dt, J=1.5, 14.3 Hz, 1H, —CH—$\overline{\text{C}}$=C—C(=O)).

EXAMPLE 9

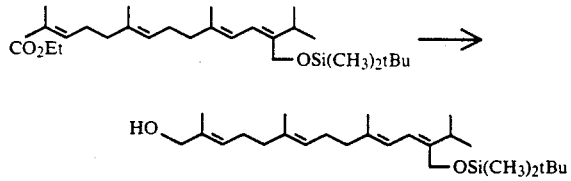

To a solution of the ester compound shown above (125 mg, 0.27 mmol), which was dissolved in toluene (5 ml) and chilled at −70° C. under argon atmosphere, was dropwise added 1.02M solution of diisobutylaluminum hydride in toluene (0.64 ml, 0.65 mmol), and the resultant mixture was stirred at the same temperature for 30 minutes. Addition of water (0.3 ml) stopped the reaction. The reaction mixture was vigorously stirred at room temperature for 1 hour, and resultant precipitates were filtered off. The filtrate was concentrated to give the objective allyl compound (100 mg, 88%).

IR (film) cm$^{-1}$; 3350, 2970, 2945, 2870, 1462, 1252, 1080, 1055, 835, 773.

$^1$HNMR (CDCl$_3$, 250 MHz) δ ppm: 0.08 (s, 6H, (CH$_3$)$_2$Si), 0.91 (s 9H, (CH$_3$)$_3$Si), 1.07 (d, J=6.8 Hz, 6H, (C$\overline{\text{H}}$$_3$)$_2$CH), 1.26 (brs, 1H, OH), 1.62, 1.67, 1.80 (each s, each 3H, CH$_3$— C=C), 1.95–2.20 (m, 8H, —CH$_2$—CH$_2$—x2), 2.54 (hep, J=6.8 Hz, 1H, (CH$_3$)CH—), 3.99 (brs, 1H, CH$_2$OH), 4.30 (s, 2H, CH$_2$OSi), 5.14 (m, 1H, —C=CH—CH$_2$—), 5.39 (brt, J=6.3 Hz, 1H, —C=C$\overline{\text{H}}$—CH$_2$—), 6.10 (s, 2H, —C=CH—CH=C—).

EXAMPLE 10

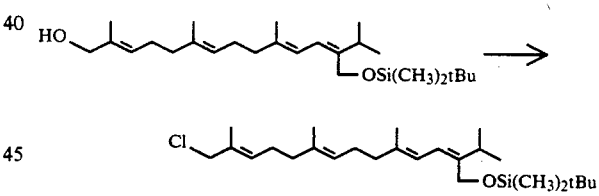

To a solution of the allyl alcohol compound shown above (100 mg, 0.24 mmol), which was dissolved in carbon tetrachloride (1 ml), was added triphenyl phosphine (71 mg, 0.27 mmol), and the mixture was refluxed for 6 hours. After cooling, the mixture was concentrated under reduced pressure. The residue was mixed with n-hexane (30 ml), and precipitates were filtered off. The filtrate was concentrated and the residue was chromatographed on a silica gel column to give the objective chlorinated compound (92 mg, 95%).

IR (film) cm$^{-1}$; 3080, 3060, 2970, 2940, 2860, 1435, 1260, 1080, 835, 775, 742, 695.

$^1$HNMR (CDCl$_3$) δ ppm: 0.08 (s, 6H, (CH$_3$)$_2$Si), 0.91 (s, 9H, (CH$_3$)$_3$CSi), 1.07 (d, J=6.9 Hz, 6H, (CH$_3$)$_2$CH), 1.61, 1.73, 1.76 (each s, each 3H, CH$_3$C=C), $\overline{1.}$95–2.20 (m, 8H, —CH$_2$—CH$_2$—), 2.54 (hep, J=6.9 Hz, 1H, (CH$_3$)$_2$CH—), 4.01, 4.30 (each s, each 2H, CH$_2$Cl, CH$_2$OSi), 5.14 (m, 1H, C=CH— CH$_2$—), 5.50 (brt, J=6.5 Hz, C=CH—CH$_2$—), $\overline{6.}$10 (s, 2H, C=CH—CH=C).

REFERENCE EXAMPLE 1

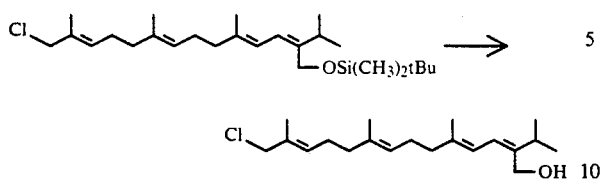

To a solution of the chlorinated compound shown above (92 mg, 0.23 mmol), which was dissolved in tetrahydrofuran (1 ml), was added 1.0M solution of tetrabutylammonium chloride in tetrahydrofuran (0.30 ml, 0.30 mmol) at room temperature, and the resultant mixture was stirred at the same temperature for 1 hour. The reaction mixture was mixed with ethyl acetate (10 ml)-saturated brine (5 ml), and the organic layer was dried over anhydrous magnesium sulfate and concentrated. The residue was chromatographed on a silica gel column to give the objective hydroxy compound (66 mg, 88%).

IR (film) cm$^{-1}$; 3360, 2980, 2940, 2890, 1445, 1385, 1265, 1010.

$^1$HNMR (CDCl$_3$ 250 MHz) δ ppm: 1.06 (d, J=6.8 Hz, 6H, —CH(CH$_3$)$_2$), 1.58, 1.70, 1.75 (each br, each 3H, —CH=CCH$_3$—), 1.9-2.2 (m, 8H, —CH$_2$CH$_2$—), 2.47 (hep, J=6.8 Hz, 1H, —CH(CH$_3$)$_2$), 3.98 (bs, 2H, —CH$_2$Cl), 4.23 (bs, 2H, —C$_2$OH), 5.09 (m, 1H, —C=CHCH$_2$—), 5.47 (bt, J=6.7 Hz, —C=CHCH$_2$—), 6.13, 6.16 (each d, J=12.0 Hz, each 1H, —C=CH—CH=C—).

REFERENCE EXAMPLE 2

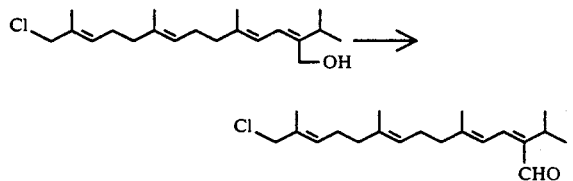

The allyl alcohol compound shown above [14-chloro-2-(1-methylethyl)-5,9,13-trimethyl-2,4,8,12-tetradecatetraen-1-ol] (492 mg, 1.51 mmol) obtained in Reference Example 1 was dissolved in methylene chloride (22 ml). To the solution was added powdery barium manganate (8.5 g), and the resultant mixture was stirred under argon atmosphere. Disappearance of the starting material was confirmed eight hours later, and the mixture was filtered and washed. The filtrate and washings were combined and concentrated. The residue was chromatographed on a silica gel column (Eluent:n-hexane:ethyl acetate=15:1) to give the objective 14-chloro-2-(1-methylethyl)-5,9,13-trimethyl-2,4,8,12-tetradecatetraenal (468 mg, 95%).

IR (film) cm$^{-1}$; 2970, 2930, 2880, 1670, 1630, 1445, 1390, 1295, 1265, 1135.

$^1$HNMR (CDCl$_3$, 250 MHz) δ ppm: 1.04 (d, J=7.0 Hz, 6H, —CH(CH$_3$)$_2$), 1.59, 1.70 (each bs, each 3H, —C=CCH$_3$), 1.87 (d, J=1.3 Hz, 3H, —C=CCH$_3$), 1.9—2.2 (m, 8H, —CH$_2$—CH$_2$), 2.89 (hep, J=7.0 Hz, 1H, —CH(CH$_3$)$_2$), 3.98 (bs, 2H, —CH$_2$Cl), 5.09 (m, 1H, —C=CHCH$_2$—), 5.47 (bt, J=6.5 Hz, 1H, —C=CHC-H$_2$—), 6.82 (d, J=12.0 Hz, 1H, —C=CH—CH=C(-CHO)—), 7.11 (d, J=12.0 Hz, —C=CH—CH=C(-CHO)—), 10.27 (s, 1H, —CHO).

REFERENCE EXAMPLE 3

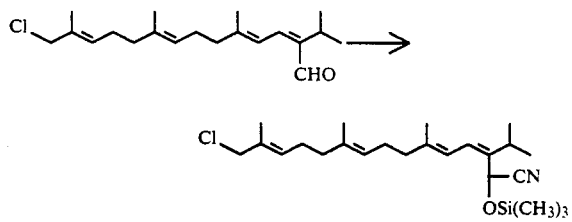

The formyl compound shown above [14-chloro-2-(1-methylethyl)-5,9,13-trimethyl-2,4,8,12-tetradecatetraenal] (640 mg, 2.0 mmol) was dissolved in trimethylsilylnitrile (0.35 ml, 2.6 mmol). To the solution was added a very small amount of potassium cyanide/18-crown 6-ether complex with stirring on an ice water bath under nitrogen atmosphere. Disappearance of the starting material was confirmed 2 hours later, and the excessive trimethylsilylnitrile was distilled off to give crude 15-chloro-3-(1-methylethyl)-6,10,14-trimethyl-2-(trimethylsiloxy)-3,5,9,13-pentadecatetraenenitrile (647 mg, quantitatively).

IR (film) cm$^{-1}$; 2960, 2930, 2880, 2320, 1445, 1255, 1080, 875, 845.

$^1$HNMR (CDCl$_3$, 250 MHz) δ ppm: 1.11, 1.15 (each d, J=6.9 Hz, each 3H, —CH(CH$_3$)$_2$), 1.60, 1.71, 1.77 (each s, each 3H, —C=CCH$_3$), 1.9-2.2 (m, 8H, —CH$_2$CH$_2$—), 2.64 (hep, J=6.9 Hz, 1H, —CH(CH$_3$)$_2$), 3.99 (s, 1H, —CH$_2$Cl), 5.11 (m, 1H, —C=CHCH$_2$—), 5.33 (s, 1H, —CHCN), 5.48 (bt, J=6.5 Hz, 1H, —C=CHCH$_2$)—), 6.04, 6.25 (each d, J=11.3 Hz, each 1H, —C=CH—CH=C—.

REFERENCE EXAMPLE 4

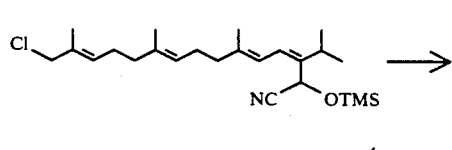

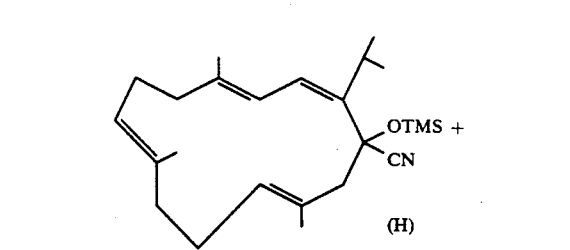

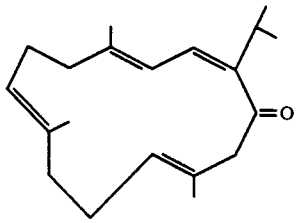

To a solution of lithium hexamethyldisilazide in tetrahydrofuran (20 ml, 5.0 mmol, 0.25M) was dropwise added with stirring on an oil bath at 55° C. under argon atmosphere a solution of 15-chloro-3-(1-methylethyl)-

6,10,14-trimethyl-2-trimethylsiloxy-3,5,9,13-pentadecatetraenenitrile (378 mg, 0.895 mmol) in tetrahydrofuran (15 ml) in 50 minutes. The resultant mixture was stirred at this temperature for 20 minutes and poured into a mixture of saturated brine (30 ml)-hexane (20 ml) containing ice (50 g) for stopping the reaction. The organic layer was separated, and the aqueous layer was extracted with hexane-ether (5:1, 30 ml). The extract was dried over sodium sulfate and concentrated under reduced pressure. The resultant residue was chromatographed on a silica gel column to give 2-(1-methylethyl)-5,9,13-trimethyl-1-trimethylsiloxy-2,4,8,12-cyclotetradecatetraen-1-carbonitrile (H) (288 mg, 83%) and 2-(1-methylethyl)-5,9,13-trimethyl-2,4,8,12-cyclotetradecatetraen-1-one (42.9 mg, 0.11 mmol, 16%).

Compound (H) had the following physico-chemical properties.

IR (film) cm$^{-1}$; 2970, 2920, 1440, 1385, 1253, 1125, 1085, 940, 845, 755.

$^1$HNMR (CDCl$_3$, 250 MHz) δ ppm; 0.23 (s, 9H, —SiMe$_3$), 1.09, 1.15 (each d, J=6.7 Hz, each 3H, —CH(CH$_3$)$_2$), 1.50, 1.62 (each bs, each 3H, —C=CCH$_3$), 1.70 (d, J=1.3 Hz, 3H, —C=CCH$_3$), 2.0–2.2 (m, 8H, —CH$_2$CH$_2$—x2), 2.51 (sep, J=6.7 Hz, 1H, —CH(CH$_3$)$_2$), 2.55, 2.65 (each d, J=14.2 Hz, each 1H, —CHaHbCN—), 4.94 (bt, J=6.1 Hz, 1H, 1H, —C=CHCH$_2$—), 5.15 (bt, J=5.6 Hz, 1H, —C=CHCH$_2$—), 6.17, 6.44 (each d, J=11.8 Hz, each 1 H, —C=CH—CH=C—).

REFERENCE EXAMPLE 5

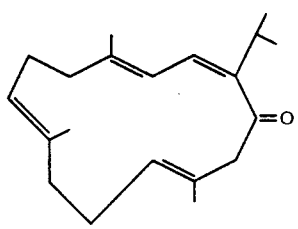

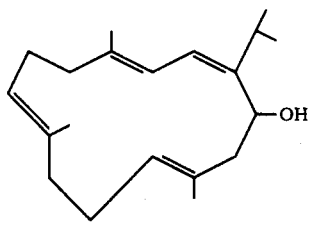

The ketone compound shown above [2-(1-methylethyl)-5,9,13-trimethyl-2,4,8,12-cyclotetradecatetraen-1-one] (137 mg, 0.48 mmol) was dissolved in dry toluene (2.5 ml). To the solution was added with stirring on a cold bath at −70° C. under argon atmosphere 1M solution of diisobutylaluminum hydride in toluene (0.6 ml). Disappearance of the starting material was confirmed 1 hour later, and the mixture was mixed with 0.25 ml of water. The bath was removed, and the mixture was stirred well, dried over anhydrous magnesium sulfate, stirred, and filtered. The filtrate was concentrated. The residue was chromatographed on a silica gel column (Eluent: n-hexane:ethyl acetate=12:1) to give sarcophytol A (125 mg, 88%).

What is claimed is

1. A conjugated diene compound of the formula (I):

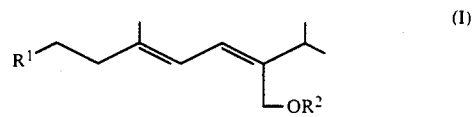

wherein R$^1$ is

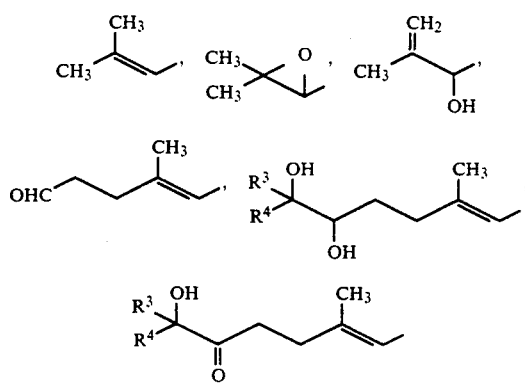

(in which R$^3$ and R$^4$ are independently alkyl group of 1 to 4 carbon atoms or taken together form a cyclic alkyl group),

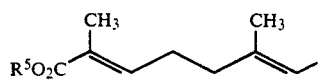

(in which R$^5$ is alkyl group of 1 to 4 carbon atoms) or

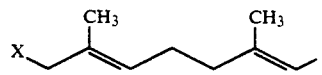

(in which X is hydroxy group, halogen atom or —O-SO$_2$R$^6$ (R$^6$ is alkyl group of 1 to 4 carbon atoms optionally substituted by halogen atom or phenyl group optionally substituted by alkyl group of 1 to 4 carbon atoms)), and R$^2$ is hydrogen atom,

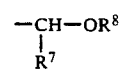

(in which R$^7$ is hydrogen atom or alkyl group of 1 to 4 carbon atoms, R$^8$ is alkyl group of 1 to 4 carbon atoms, or R$^7$ and R$^8$ taken together may form a ring),

(in which R$^9$–R$^{11}$ are independently alkyl group of 1 to 4 carbon atoms or phenyl group) or acyl group, with the proviso that when R$^1$ is

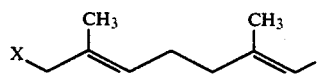

(X is as defined above), R$^2$ is not hydrogen atom.

* * * * *